United States Patent [19]

Sikorski et al.

[11] Patent Number: 4,508,663

[45] Date of Patent: * Apr. 2, 1985

[54] PROCESS FOR PREPARING THIOSULFENAMIDE DERIVATIVES OF N-PHOSPHONOMETHYLGLYCINONITRILES

[75] Inventors: James A. Sikorski, West Lafayette, Ind.; Mary A. Hoobler, Creve Coeur, Mo.

[73] Assignee: Monsanto Company, St. Louis, Mo.

[*] Notice: The portion of the term of this patent subsequent to Aug. 30, 2000 has been disclaimed.

[21] Appl. No.: 514,403

[22] Filed: Jul. 18, 1983

Related U.S. Application Data

[62] Division of Ser. No. 309,321, Oct. 5, 1981, Pat. No. 4,407,763.

[51] Int. Cl.$^3$ ............................................. C07F 9/32
[52] U.S. Cl. ............................................. 260/968
[58] Field of Search .................. 260/968; 549/221

[56] References Cited

U.S. PATENT DOCUMENTS

| | | | |
|---|---|---|---|
| 4,008,296 | 2/1977 | Barton | 260/940 |
| 4,067,719 | 1/1978 | Dutra | 71/86 |
| 4,252,554 | 2/1981 | Dutra | 71/87 |
| 4,401,604 | 8/1983 | Sikorski et al. | 260/968 |

OTHER PUBLICATIONS

Unverified translation of Japanese Patent 142,047, Nov. 1977.

Primary Examiner—Anton H. Sutto
Attorney, Agent, or Firm—Raymond C. Loyer; Richard H. Shear; Gordon F. Sieckmann

[57] ABSTRACT

This invention relates to a process for preparing sulfenyl chloride derivatives of N-phosphonomethylglycinonitriles which are useful as herbicides or as intermediates for the production of thiosulfenamide derivatives of N-phosphonomethylglycinonitriles which are useful as herbicides.

26 Claims, No Drawings

PROCESS FOR PREPARING THIOSULFENAMIDE DERIVATIVES OF N-PHOSPHONOMETHYLGLYCINONITRILES

This is a division of application Ser. No. 309,321, filed Oct. 5, 1981, now U.S. Pat. No. 4,407,763.

This invention relates to a process for preparing sulfenyl chloride derivatives of N-phosphonomethylglycinonitriles which are useful as herbicides or as intermediates for the production of thiosulfenamide derivatives of N-phosphonomethylglycinonitriles which are useful as herbicides.

U.S. Pat. No. 4,067,719 issued to Gerard A. Dutra on Jan. 10, 1978 discloses N-phosphonomethylglycinonitriles of the formula

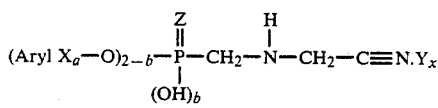

wherein (Aryl) is selected from phenyl, naphthyl or biphenylyl, each X is a substituent on said Aryl selected from halogen, alkyl of 1 to 4 carbons, alkoxy and alkylthio of 1 to 3 carbons, alkoxycarbonyl of 2 to 3 carbon atoms, methylenedioxy, cyano, trifluoromethyl or nitro, Z is oxygen or sulfur, a is an integer from zero to 3, b is an integer from zero to 1, Y is a strong acid capable of forming a salt with the amino group, and x is zero or 2, provided that x must be zero when b is 1, as well as a process for producing such compounds. These N-phosphonomethylglycinonitriles are said to be useful as herbicides.

U.S. Pat. No. 4,008,296 issued to John Edward D. Barton on Feb. 15, 1977 describes ester derivatives of N-phosphonomethylglycinonitrile having the formula

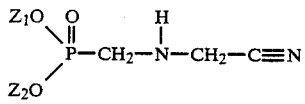

wherein $Z_1$ and $Z_2$ each represent an alkyl radical of from 1 to 6 carbon atoms; which are said to be useful as herbicides.

Japanese L.O.P. No. 142047/1977 discloses phenylcyanomethylaminomethylphosphonates of the formula

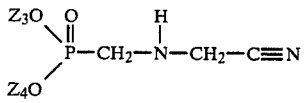

wherein $Z_3$ is hydrogen or phenyl and $Z_4$ is phenyl. Japanese L.O.P. No. 93323/1974 describes the preparation of N-(diethylphosphonomethyl)aminoacetonitrile.

U.S. Pat. No. 4,252,554 issued to Gerard A. Dutra et al on Feb. 24, 1981 discloses compounds represented by the formula

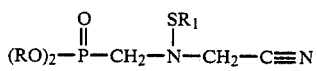

wherein R is phenyl, naphthyl or biphenylyl or phenyl, naphthyl or biphenylyl substituted with from 1 to 3 substituents independently selected from the group consisting of lower alkyl, lower alkoxy, lower alkylthio, alkoxycarbonyl, methylenedioxy, trifluoromethyl, cyano, nitro and halogen; and $R_1$ is phenyl or phenyl substituted with from 1 to 3 substituents independently selected from the group consisting of lower alkyl, lower alkoxy, halogen, trifluoromethyl and nitro.

In accordance with the present invention, thiosulfenamide derivatives of N-phosphonomethylglycinonitriles of the formula

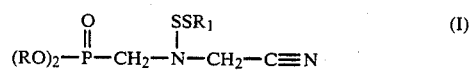

wherein R is selected from the group consisting of phenyl, naphthyl, biphenylyl; or phenyl, naphthyl or biphenylyl substituted with from 1 to 3 substituents independently selected from the group consisting of lower alkyl, lower alkoxy, lower alkylthio, alkoxycarbonyl, methylenedioxy, trifluoromethyl, cyano, nitro and halogen; and $R_1$ is independently alkyl, cycloalkyl, aralower alkyl, phenyl, naphthyl, or phenyl, naphthyl or aralower alkyl substituted with from 1 or 3 substituents selected from the group consisting of lower alkyl, lower alkoxy, halogen, and trifluoromethyl, are prepared by reacting a compound of the formula

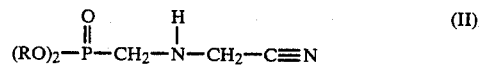

wherein R is as aforedefined with sulfur dichloride in an aprotic solvent and in the presence of a hydrogen chloride acceptor to form a compound of the formula

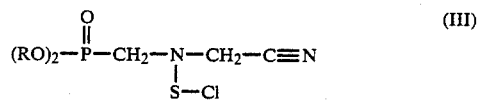

wherein R is as aforedefined.

The reaction temperature for the aforerecited reaction is in the range from about −50° C. to about 100° C., and is preferably from about −30° C. to about +10° C., although greater or lower temperatures may be employed if desired when practicing the process of this invention.

It is preferred to add a compound of formula (II) to the sulfur dichloride rather than vice versa so as to minimize the possibility of having excess compound of formula (II) in the presence of sulfur dichloride whereby bis glyphosate adduct an undesired coproduct could be formed.

In preparing the compounds of formula (III), the ratio of reactants of formula (II) and sulfur dichloride, is not narrowly critical. For best results, however, for each mole of a compound of formula (II), one should employ one mole of sulfur dichloride to produce one mole of a compound of formula (III). It is preferred to employ an excess of sulfur dichloride for ease of reaction and maximum yield of product of formula (III). The 2:1 adduct byproduct and an amine hydrochloride formed along with a compound of formula (III) are generally separated therefrom as a precipitate.

The compound of formula (III) is reacted with a thiol compound of the formula

wherein $R_1$ is as aforedefined, in the presence of a hydrogen chloride acceptor to form a compound of formula (I).

In reacting compounds of formula (III) with compounds of formula (IV), the temperature is in the range from about $-30°$ C. to about $100°$ C. and is preferably from about $-10°$ C. to about $+30°$ C. although greater or lower temperatures may be employed if desired.

The ratio of compounds of formula (III) and (IV) is not critical. For best results, however, one should employ for each mole of a compound of formula (III) a mole of a compound of formula (IV). Typically a molar excess of compound of formula (IV) is employed.

Typical compounds which may be employed as a compound of formula (IV) include thiol compounds such as methyl, ethyl, butyl, isopropyl, isopentyl, t-butyl, octyl, cyclohexyl, phenylethyl, naphthy mercaptans, and thiophenols substituted with lower alkoxy, trifluoromethy, lower alkyl, and halogen.

It is preferred that R is phenyl. Also it is preferred that $R_1$ is independently alkyl such as methyl, isopropyl, isopentyl, t-butyl, octyl; cycloalkyl such as cyclohexyl; naphthyl; or phenyl substituted with lower alkoxy, trifluoromethyl, halogen or lower alkyl.

Illustrative of the substituted phenyl groups which R and $R_1$ independently represent are mono-substituted phenyl wherein the substituent is in the ortho, meta or para position, for example, methylphenyl, butylphenyl, methoxyphenyl, butoxyphenyl, fluorophenyl, chlorophenyl, bromophenyl, iodophenyl, trifluoromethylphenyl, nitrophenyl, methylthiophenyl, butylthiophenyl, cyanophenyl, ethoxycarbonylphenyl, and the like, and the di- and tri-substituted phenyl groups wherein the substituents are the same or different and are located in the 2, 3, 4, 5 or 6 positions of the phenyl ring, for example, dichlorophenyl, dimethylphenyl, methylchlorophenyl, ethylfluorophenyl, dibutoxyphenyl, butylnitrophenyl, methylthiochlorophenyl, di(ethylthio)phenyl, trimethylphenyl, trichlorophenyl, tributylphenyl, ethyldichlorophenyl and the like.

Groups representative of a substituted naphthyl groups represented by R include methylnaphthyl, nitronaphthyl, bromonaphthyl, dimethylnaphthyl, difluoronaphthyl, trimethylnaphthyl and the like.

Groups representative of substituted biphenylyl groups represented by R include methyldiphenylyl, nitrobiphenylyl, bromobiphenylyl, dimethylbiphenylyl, difluorobiphenylyl, trimethylbiphenylyl and the like.

As employed herein, the term "lower alkyl" designates alkyl radicals which have from 1 to 4 carbon atoms in a straight or branched chain, for example, methyl, ethyl, propyl, isopropyl, butyl, isobutyl, sec-butyl, and t-butyl.

As employed herein, the term "tertiary alkyl" includes alkyl and substituted alkyl radicals having 4 to 8 carbon atoms therein. Typically tertiary alkyl groups include tertiary butyl, tertiary amyl and tertiary hexyl.

As employed herein, the term "aralower alkyl" includes combinations of those groups as aforedefined for the term "lower alkyl" with aryl groups such as phenyl, benzyl, naphthyl and biphenylyl.

The term "halo" or "halogen" as employed herein means chlorine, bromine, iodine and fluorine.

The term "lower alkoxy" includes groups representative of the term "lower alkyl" in combination with oxygen and includes methoxy, ethoxy, propoxy, butoxy mixtures thereof and the like.

The term "lower alkylthio" includes representatives of lower alkyl in combination with sulfur.

The term "lower alkoxycarbonyl" includes groups representative of the aforedefined term "lower alkoxy" in combination with a carbonyl group.

The hydrogen chloride acceptor is typically an amine, preferably a tertiary amine, which will not react with the reactants employed or products formed. Examples of suitable tertiary amine hydrogen chloride acceptors include trimethylamine, triethylamine, tributylamine, trihexylamine, 1,5-diazabicyclo-[5.4.0]-undec-5-ene, pyridine, quinoline, mixtures thereof and the like.

Due to the reactive nature of the various reaction intermediates and reactants, the process of the present invention should be conducted in an aprotic solvent under essentially anhydrous conditions. Illustrative of the aprotic solvents employed in the process of this invention include benzene, toluene, dichloromethane, tetrahydrofuran, cyclohexane, methylcyclohexane, hexane, octane, dioxane, ethyl ether and the like, although a solvent is not required.

While the processes of this invention can be conducted at atmospheric, sub-atmospheric or super-atmospheric pressure, for convenience and economy it is generally preferred to conduct these processes at atmospheric pressure.

The following illustrative, non-limiting examples will serve to further demonstrate to those skilled in the art the manner in which specific compounds within the scope of this invention can be prepared. In the examples, all parts are parts by weight unless otherwise expressly stated.

Groups typical of the term "aralower alkyl" include phenylmethyl, phenylethyl, phenylpropyl, phenylbutyl and the like.

The term "alkyl" is herein defined to mean a substituted or unsubstituted monovalent radical in a straight or branched chaim of the formula $C_nH_{2n+1}H-$, wherein n is an integer from 1 to 8.

The term "cycloalkyl" is herein defined to mean carbon and hydrogen atoms arranged in a cyclic or ring arrangement having 3 to 8 carbon atoms therein such as cyclopropyl, cycloheptyl, cyclooctyl, cyclohexyl and the like.

EXAMPLE I

Phosphonic acid, [[(cyanomethyl)-N-chlorothio]amino]methyl]-,diphenyl ester. A solution of diphenyl-N-phosphonomethylglycinonitrile (4.5 g, 0.015 mol) and triethylamine (1.5 g, 0.015 mol) in toluene was added to a pentane solution of sulfur dichloride (1.5 g, 0.015 mol) at 0° at such a rate that the temperature did not exceed $+10°$ C. The yellow reaction mixture was stirred at 0° C. for 45 minutes. The supernatant liquid was removed under nitrogen and concentrated in vacuo to a yellow oil which became light brown upon drying overnight on a vacuum pump. Yield 4.4 g (79%), $^{31}P$ NMR ($-11.15$ ppm) having an analysis for $C_{15}H_{14}Cl_1N_2O_3P_1S_1$:

Calculated C,48.85; H,3.83; N,7.60; S,8.69; Cl,9.61;
Found: C,48.78; H,3.88; N,7.53; S,8.75; Cl,9.51.

General Procedure For The Preparation Of Glyphosate thiosulfenamides from phosphonic acid, [[(cyanomethyl)-N-chlorothio]amino]methyl]-diphenyl ester For Examples II, III, IV, V, VI, VII and VIII hereafter following To an oven-dried 500 ml flask, cooled under nitrogen, was added 250 ml of toluene, triethylamine (0.025 mol), and the appropriate mercaptan (0.025 mol). The resulting solution was cooled to 0° C. Then a toluene solution containing phosphonic acid, [[(cyanomethyl)-N-chlorothio]amino]methyl]-diphenyl ester (0.025 mol) was added slowly via double-ended needle under nitrogen at such a rate that the reaction temperature was maintained below 10° C. When the addition was complete, the reaction mixture was stirred for 2 hours at +10° C. and then allowed to come to room temperature. The precipitate of triethylamine hydrochloride was removed by filtration. The toluene filtrate was washed with cold 10% aqueous sodium hydroxide, cold water, dried over $MgSO_4$, filtered, adsorbed onto silica gel and purified by HPLC on a 1"×4' silica gel column to give the desired glyphosate thiosulfenamides. $^1H$ and $^{31}P$ NMR, FDMS, and elemental analyses are all consistent with pure products.

EXAMPLE II

Phosphonic acid, [[(cyanomethyl)(octyldithio)amino]methyl]-, diphenyl ester corresponding to a compound of formula (I) wherein R is phenyl and $R_1$ is 1-octyl was prepared using the aforerecited procedure as a brown oil having a refractive index $n_D^{25.7}=1.5478$ and an analysis for $C_{23}H_{31}N_2O_3PS_2$:

Calculated: C,57.72; H,6.53; N,5.85; S,13.39; Found: C,58.72; H,6.39; N,5.70; S,13.01.

EXAMPLE III

Phosphonic acid, [[(cyanomethyl)[(4-methoxyphenyl)-dithio]amino]methyl]-, diphenyl ester corresponding to a compound of formula (I) wherein R is phenyl and $R_1$ is 4-methoxyphenyl was prepared using the aforerecited procedure as a yellow oil having a refractive index $n_D^{23.4}=1.6040$ and an analysis for $C_{22}H_{21}N_2O_4PS_2$:

Calculated: C,55.92; H,4.48; N,5.93; S,13.57; Found: C,55.84; H,4.52; N,5.87; S,13.62.

EXAMPLE IV

Phosphonic acid, [[(cyanomethyl)[[3-(trifluoromethyl)phenyl]dithio]amino]methyl]-, diphenyl ester corresponding to a compound of formula (I) wherein R is phenyl and $R_1$ is 3-trifluoromethylphenyl was prepared using the aforerecited procedure as a yellow oil having a refractive index $n_D^{25.2}=1.5666$ and an analysis for $C_{22}H_{18}F_3N_2O_3PS_2$:

Calculated: C,51.76; H,3.55; N,5.49; S,12.56; Found: C,51.93; H,3.59; N,5.36; S,12.43

EXAMPLE V

Phosphonic acid, [[(cyanomethyl)[(3-methylbutyl)dithio]amino]methyl]-, diphenyl ester corresponding to a compound of formula (I) wherein R is phenyl and $R_1$ is 3-methylbutyl was prepared using the aforerecited procedure as a light yellow oil having a refractive index $n_D^{24.5}=1.5593$ and an analysis for $C_{20}H_{25}N_2O_3PS_2$:

Calculated: C,55.03; H,5.77; N,6.42; S,14.69; Found: C,55.02; H,5.80; N,6.43; S,14.63.

EXAMPLE VI

Phosphonic acid, [[(cyanomethyl)[(1-methylethyl)dithio]amino]methyl]-, diphenyl ester corresponding to a compound of formula (I) wherein R is phenyl and $R_1$ is 1-methylethyl, (or isopropyl) was prepared using the aforerecited procedure as a light yellow oil having a refractive index $n_D^{24.8}=1.5689$ and an analysis for $C_{18}H_{21}N_2O_3PS_2$:

Calculated: C,52.93; H,5.18; N,6.86; S,15.70; Found: C,53.02; H,5.23; N,6.80, S,15.60.

EXAMPLE VII

Phosphonic acid, [[(cyanomethyl)[(methyldithio]amino]methyl]-, diphenyl ester corresponding to a compound of formula (I) wherein R is phenyl and $R_1$ is methyl was prepared using the aforerecited procedure as a yellow oil having a refractive index $n_D^{25}=1.5759$ and an analysis for $C_{16}H_{17}N_2O_3PS_2$:

Calculated: C,50.52; H,4.50; N,7.36; S,16.86 Found: C,50.62; H,4.53; N,7.35; S,l16.80.

EXAMPLE VIII

Phosphonic acid, [[(cyanomethyl)[[3-(trifluoromethyl)phenyl]methyl]dithio]amino]methyl]-, diphenyl ester corresponding to a compound of formula (I) wherein R is phenyl and $R_1$ is 3-trifluoromethylphenylmethyl was prepared using the aforerecited procedure as a yellow oil having a refractive index $n_D^{24.40}=1.5640$ and an analysis for $C_{23}H_{20}F_3N_2O_3PS_2$:

Calculated: C,52.67; H,3.84; N,5.34; S,12.23; Found: C,52.57; H,3.84; N,5.32; S,12.20.

General Procedure For The Preparation Of Glyphosate thiosulfenamides from phosphonic acid, [[(cyanomethyl)-N-chlorothio]amino]methyl]-diphenyl ester For Examples IX, X, XI and XII hereafter following To an oven-dried 500 ml flask, cooled under nitrogen, is added 250 ml of toluene and cooled in an ice bath. The appropriate mercaptan and 2-3 equivalents of triethylamine was added. To this solution was added slowly via double-ended needle a toluene solution of phosphonic acid, [[(cyanomethyl)-N chlorothio]amino]methyl]-diphenyl ester maintaining the temperature below 10° C. The reaction mixture was stirred for 3-4 hours while allowing to warm to room temperature. The triethylamine hydrochloride was removed by filtration and the filtrate was washed with cold 10% aqueous sodium hydroxide, cold water, dried over $MgSO_4$, filtered, adsorbed onto silica gel. Purification by HPLC on a 1"×4' silica gel column eluting with 30-40% ethylacetate/cyclo-hexane gave the desired thiosulfenamides. $^1H$ and $^{31}P$ NMR, FDMS, and elemental analyses are all consistent with pure products.

EXAMPLE IX

Phosphonic acid, [[(cyanomethyl)(2-naphthalenyldithio)amino]methyl]-, diphenyl ester corresponding to a compound of formula (I) wherein R is phenyl and $R_1$ is 2-naphthyl was prepared using the aforerecited procedure as a light yellow solid having a melting point of 72°-75° C. and an analysis for $C_{25}H_{21}N_2O_3PS_2$:

Calculated: C,60.96; H,4.30; N,5.69; S,13.02; Found: C,61.00; H,4.34; N,5.65; S,12.96.

EXAMPLE X

Phosphonic acid, [[(cyanomethyl)(cyclohexyldithio)amino]methyl]-, diphenyl ester corresponding to a compound of formula (I) wherein R is phenyl and $R_1$ is cyclohexyl was prepared using the aforerecited procedure as a brown oil having a refractive index $n_D^{24.2} = 1.5741$ and an analysis for $C_{21}H_{25}N_2O_3PS_2$:

Calculated: C,56.36; H,5.41; N,6.26; S,14.33; Found: C,56.17; H,5.48; N,6.21; S,14.25.

EXAMPLE XI

Phosphonic acid, [[(4-chlorophenyl)dithio](cyanomethyl)amino]methyl]-, diphenyl ester corresponding to a compound of formula (I) wherein R is phenyl and $R_1$ is 4-chlorophenyl was prepared using the aforerecited procedure as a brown solid having a melting point of 50°-55° C. and an analysis $C_{21}H_{18}ClN_2O_3PS_2$:

Calculated: C,52.89; H,3.81; N,5.87; S,13.44; Found: C,52.65; H,3.91; N,5.83; S,13.36.

EXAMPLE XII

Phosphonic acid, [[(cyanomethyl)[(2-phenylethyl)dithio]amino]methyl]-, diphenyl ester corresponding to a compound of formula (I) wherein R is phenyl and $R_1$ is 2-phenylethyl was prepared using the aforerecited procedure as a brown oil having a refractive index $n_D^{25} = 1.5948$ and an analysis for $C_{23}H_{23}N_2O_3PS_2$:

Calculated: C,58.71; H,4.93; N,5.95; S,13.63; Found: C,58.48; H,4.98; N,5.92; S,13.56.

EXAMPLE XIII

An oven-dried 500 ml flask cooled under nitrogen was charged with 150 ml of toluene, cooled to −20° C., and sulfur dichloride (5.1 g, 0.05 mol) was added. To this solution was added slowly via cannula a solution of diphenylphosphonomethylglycinonitrile (15 g, 0.05 mol) and excess triethylamine in 150 ml of toluene, at such a rate to maintain the temperature below −10° C. The reaction mixture was stirred at −20° C. for 3 hours. The supernatant liquid, a toluene solution of phosphonic acid, [[(cyanomethyl)-N-chlorothio-amino)methyl]-, diphenyl ester was removed under nitrogen and added slowly via cannula over a 2 hour period to a solution of tert-butyl mercaptan (4.5 g, 0.05 mol) and excess triethylamine in 100 ml of toluene at −20° C. After 30 minutes the precipitate of triethylamine hydrochloride was removed by filtration and the filtrate was washed with cold 10% aqueous NaOH followed by cold water, dried over $MgSO_4$, filtered, and concentrated in vacuo. Purification by HPLC on a Waters Prep Pak 500 silica gel column, eluting with 20% ethyl acetate, 80% cyclohexane, followed by recrystallization from methylene chloride, petroleum ether gave 3.3 g of tan solid, having a melting point of 87°-88° C., corresponding to a compound of formula (I) wherein R is phenyl and $R_1$ is tertiary butyl and having an analysis $C_{19}H_{23}N_2O_3PS_2$:

Calculated: C,54.01; H,5.49; N,6.63; S,15.15; Found: C,53.93; H,5.52; N,6.60; S,15.13.

Other compounds which are believed preparable by the process of this invention include but are not limited to phosphonic acid, [[(cyanomethyl)[(1,1-dimethylethyl)-dithio]amino]methyl]-, diphenyl ester; phosphonic acid, [[(cyanomethyl)[(1,1-dimethylethyl)-dithio]amino]methyl]-, bis(4-methoxyphenyl)) ester; phosphonic acid, [[(cyanomethyl)[(1,1-dimethylethyl)-dithio]amino]methyl]-, bis(4-chloro-3-methylphenyl ester; phosphonic acid, [[(cyanomethyl)[(1,1-dimethylpropyl)dithio]amino]methyl]-, diphenyl ester; and phosphonic acid, [[(cyanomethyl)[(1,1-dimethylethyl)-dithio]amino]methyl]-,bis(2-methoxyphenyl)ester; and phosphonic acid, [[(cyanomethyl)[(4-methylphenyl)dithio]amino]methyl]-, diphenyl ester.

EXAMPLE XIV

The post-emergence herbicidal activity of some of the various compounds of this invention was demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm² absolute. The atomizer contains 6 ml. of a solution or suspension of the chemical. In that 6 ml., is an amount of a cyclohexanone emulsifying agent mixture to give a spray solution or suspension which contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the two-week observations are omitted.

The post-emergence herbicidal activity index used in Table I is as follows:

| Plant Response | Index |
| --- | --- |
| 0–24% control | 0 |
| 25–49% control | 1 |
| 50–74% control | 2 |
| 75–99% control | 3 |
| 100% control | 4 |

The plant species utilized in these tests are identified by letter in accordance with the following legend:

| | |
| --- | --- |
| A — Canada Thistle* | K — Barnyardgrass |
| B — Cocklebur | L — Soybean |
| C — Velvetleaf | M — Sugar Beet |
| D — Morningglory | N — Wheat |
| E — Lambsquarters | O — Rice |
| F — Smartweed | P — Sorghum |
| G — Yellow Nutsedge* | Q — Wild Buckwheat |

-continued

H — Quackgrass*  R — Hemp Sesbania
I — Johnsongrass*  S — Panicum Spp
J — Downy Brome  T — Crabgrass

*Established from vegetative propagules.
A dash (—) in the tables indicates that the particular species was absent in the test.

Prepared and shown herbicidally efficacious in AG-2055 "Thiosulfenamide Derivatives of N-Phosphonomethylglycinonitriles" filed simultaneously herewith.

should be recognized that each individual species selected from the above tests is a representative member of a recognized family of plant species.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight

TABLE I

| Compound of Example No. | WAT | kg/h | A | B | C | D | E | F | G | H | I | J | K |
|---|---|---|---|---|---|---|---|---|---|---|---|---|---|
| I | 4 | 11.2 | 2 | 2 | 2 | 2 | 3 | 2 | 2 | 1 | 1 | 2 | 2 |
|  | 4 | 5.6 | 1 | 3 | 2 | 2 | 4 | 0 | 2 | 0 | 1 | 0 | 1 |
| II | 4 | 11.2 | 1 | 2 | 1 | 2 | 3 | 1 | 2 | 1 | 2 | 0 | 2 |
|  | 4 | 5.6 | 1 | 2 | 1 | 2 | 3 | 0 | 2 | 0 | 3 | 1 | 1 |
| III | 4 | 11.2 | 2 | 2 | 1 | 2 | 4 | 0 | 2 | 1 | 2 | 2 | 2 |
|  | 4 | 5.6 | 2 | 1 | 1 | 1 | 3 | — | 1 | 0 | 2 | 0 | 2 |
| IV | 2 | 11.2 | 1 | 2 | 0 | 1 | 3 | 1 | 1 | 0 | 1 | 0 | 2 |
|  | 4 | 11.2 | 1 | 2 | 1 | 2 | 4 | 4 | 2 | 0 | 1 | 2 | 2 |
|  | 2 | 5.6 | 1 | 1 | 0 | 1 | 3 | 0 | 1 | 1 | 2 | 1 | 2 |
|  | 4 | 5.6 | 2 | 2 | 1 | 3 | 3 | 0 | 2 | 2 | 3 | 1 | 2 |
| V | 4 | 11.2 | 1 | 3 | 0 | 2 | 3 | 3 | 2 | 2 | 3 | 2 | 3 |
|  | 4 | 5.6 | 2 | 2 | 1 | 2 | 4 | 1 | 2 | 1 | 1 | 2 | 2 |
| VI | 4 | 11.2 | 2 | 2 | 2 | 2 | 4 | 2 | 3 | 1 | 3 | 3 | 2 |
|  | 4 | 5.6 | 2 | 2 | 1 | 2 | 3 | 2 | 0 | 0 | 3 | 2 | 2 |
| VII | 4 | 11.2 | 4 | 3 | 1 | 2 | 4 | 4 | 2 | 1 | 4 | 2 | 3 |
|  | 4 | 5.6 | 4 | 2 | 1 | 2 | 3 | 2 | 2 | 2 | 3 | 3 | 2 |
| VIII | 4 | 11.2 | — | 2 | 1 | 1 | 4 | 0 | 2 | 0 | 3 | 2 | 2 |
|  | 4 | 5.6 | — | 1 | 1 | 1 | 4 | 0 | 2 | — | 3 | 1 | 2 |
| IX | 4 | 11.2 | — | 1 | 1 | 0 | 3 | 3 | 0 | 1 | 1 | 0 | 1 |
|  | 2 | 5.6 | — | 0 | 1 | 0 | 1 | 0 | 0 | 0 | 1 | 0 | 0 |
| X | 4 | 11.2 | — | 2 | 1 | 1 | 3 | 0 | 0 | 0 | 1 | 1 | 1 |
|  | 2 | 5.6 | — | 0 | 1 | 0 | 3 | 0 | 0 | 0 | 0 | 0 | 0 |
| XI | 4 | 11.2 | — | 3 | 2 | 1 | 4 | 2 | 1 | 2 | 2 | 1 | 3 |
|  | 4 | 5.6 | — | 0 | 0 | 0 | 0 | 0 | 0 | 0 | 0 | 0 | 0 |
| XII | 4 | 11.2 | — | 4 | 2 | 1 | 4 | 3 | 2 | 3 | 4 | 3 | 2 |
|  | 4 | 5.6 | — | 2 | 0 | 1 | 4 | 0 | 2 | 0 | 1 | 0 | 2 |

TABLE II

| Compound of Example No. | WAT | kg/h | L | M | N | O | P | B | Q | D | R | E | F | C | J | S | K | T |
|---|---|---|---|---|---|---|---|---|---|---|---|---|---|---|---|---|---|---|
| I | 4 | 5.6 | 2 | 0 | 1 | 1 | 3 | 2 | 2 | 2 | 2 | 4 | — | 2 | 1 | 1 | 2 | — |
|  | 4 | 1.12 | 1 | 0 | 1 | 0 | 2 | 2 | 0 | 1 | 0 | 4 | 0 | 1 | 0 | 0 | 1 | 2 |
|  | 4 | 0.28 | 1 | 0 | 0 | 0 | 1 | 2 | 0 | 0 | 0 | 2 | 1 | 1 | 1 | 0 | 0 | 0 |
| IV | 4 | 5.6 | 1 | 0 | 1 | 2 | 3 | 3 | 2 | 2 | 1 | 4 | 2 | 1 | 1 | 2 | 3 | 3 |
|  | 4 | 1.12 | 1 | 0 | 0 | 0 | 2 | 1 | 0 | 1 | 0 | 2 | 1 | 0 | 0 | 0 | 0 | 3 |
| V | 4 | 5.6 | 2 | 1 | 1 | 1 | 3 | 3 | 1 | 2 | 1 | 3 | 1 | 2 | 2 | 1 | 3 | 3 |
|  | 4 | 1.12 | 1 | 1 | 0 | 0 | 2 | 1 | 0 | 1 | 0 | 1 | 0 | 0 | 2 | 0 | 1 | 1 |
| VI | 2 | 5.6 | 1 | 0 | 1 | 0 | 2 | 2 | 1 | 1 | 1 | 3 | — | 1 | 2 | 1 | 2 | 3 |
|  | 4 | 5.6 | 1 | 1 | 1 | 0 | 3 | 3 | 1 | 1 | 1 | 3 | — | 2 | 2 | 1 | 3 | 3 |
|  | 2 | 1.12 | 0 | 0 | 1 | 0 | 1 | 1 | 0 | 1 | 0 | 3 | — | 0 | 0 | 0 | 1 | 1 |
|  | 4 | 1.12 | 0 | 0 | 0 | 0 | 1 | 1 | 0 | 0 | 0 | 3 | — | 1 | 0 | 0 | 0 | 1 |
|  | 4 | 0.28 | 0 | 0 | 0 | 0 | 0 | 0 | 0 | 0 | 0 | 0 | — | 0 | 0 | 0 | 0 | 1 |
| VII | 2 | 5.6 | 2 | 1 | 2 | 3 | 2 | 2 | 2 | 2 | 1 | 3 | — | 2 | 1 | 1 | 3 | 4 |
|  | 4 | 5.6 | 2 | 1 | 3 | 3 | 3 | 3 | 3 | 2 | 1 | 4 | — | 2 | 1 | 2 | 3 | 4 |
|  | 2 | 1.12 | 1 | 0 | 1 | 0 | 1 | 1 | 0 | 1 | 0 | 1 | — | 1 | 1 | 0 | 1 | 3 |
|  | 4 | 1.12 | 1 | 0 | 0 | 0 | 2 | 1 | 0 | 1 | 0 | 0 | — | 0 | 0 | 0 | 1 | 3 |
|  | 2 | 0.28 | 0 | 0 | 1 | 0 | 1 | 1 | 1 | 1 | 0 | 1 | — | 0 | 0 | 0 | 0 | 1 |
|  | 2 | 0.056 | 0 | 0 | 0 | 0 | 0 | 0 | 0 | 0 | 0 | 0 | — | 0 | 0 | 0 | 0 | 0 |
| IX | 2 | 5.6 | 0 | 0 | 1 | 0 | 1 | 1 | 1 | 1 | 1 | 3 | 1 | 0 | 0 | 0 | 1 | 2 |
|  | 2 | 1.12 | 0 | 0 | 0 | 0 | 0 | 0 | 0 | 0 | 0 | 0 | 0 | 0 | 0 | 0 | 0 | 0 |
|  | 2 | 0.28 | 0 | 0 | 0 | 0 | 0 | 0 | 0 | 0 | 0 | 0 | 0 | 0 | 0 | 0 | 0 | 0 |
| XI | 2 | 5.6 | 1 | 3 | 2 | 1 | 1 | 3 | 3 | 1 | 1 | 3 | 1 | 3 | 1 | 1 | 1 | 3 |
|  | 2 | 1.12 | 0 | 1 | 0 | 0 | 0 | 0 | 0 | 0 | 0 | 0 | 0 | 0 | 0 | 0 | 0 | 0 |
| XII | 4 | 5.6 | 1 | 1 | 1 | 0 | 3 | 2 | 2 | 1 | 1 | 3 | 2 | 2 | 2 | 1 | 2 | 3 |
|  | 4 | 1.12 | 0 | 0 | 0 | 0 | 1 | 0 | 0 | 0 | 0 | 0 | 0 | 0 | 0 | 0 | 0 | 0 |
|  | 2 | 0.28 | 0 | 0 | 0 | 0 | 0 | 0 | 0 | 0 | 0 | 0 | 0 | 0 | 0 | 0 | 0 | 0 |

From the test results presented in Tables I and II, it can be seen that the post-emergent herbicidal activity of the compounds of this invention is, for the most part, general in nature. In certain specific instances, however, some selectivity is demonstrated. In this regard it of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required from about 0.1 to 2.0 parts by weight of the inert liquid extender can be replaced by a corrosion inhibitor such as ethanol mercaptan, sodium thiosulfate, dodecylmono or dimercaptan or anti-foaming agent such as a dimethylpolysiloxane, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invetion to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 56.0 or more kilograms per hectare. In pre-emergent treatments, the rate of application can be from about 5.6 to about 22.4 or more kilograms per hectare. In applications for the control of aquatic plants, the active ingredients are applied in amounts of from about 1.0 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

There are several possible methods for applying liquid compositions of this invention to emerged plants. Such methods include the use of wiper systems whereby the plant to be treated is contacted with an absorbent material containing the particular liquid composition, a portion of which is thereby released onto the plant upon contact therewith. Such wiper systems typically comprise a reservoir of the liquid composition into which a portion of the absorbent material is placed and is fed therethrough. Generally, substances employable as absorbent material include substances of any shape or form capable of absorbing the liquid composition and releasing a portion of the same upon contact with the plant. Typical absorbent materials include felt, foam rubber, cellulose, nylon, sponges, hemp, cotton, burlap, polyester over acrylic, combinations thereof and the like. Forms of absorbent material include rope, twine, string, cloths, carpets, combinations thereof and the like. These forms may be assembled in any manner desired including a pipe rope wick, a wedge rope wick, a multi-rope wick and the like.

In another possible application method, liquid compositions may be selectively applied to weeds by the use of recirculating sprayer systems wherein the recirculating spray unit is mounted on a tractor or high clearance mobile equipment and the spray is directed horizontally onto the weeds growing over a crop. Spray not intercepted by the weeds is collected in a recovery chamber before contacting the crop and is reused. Roller applications may also be employed to apply liquid compositions to weeds growing over a crop.

In yet another possible application method, shielded applicators may be employed to direct the liquid composition in the form of a spray onto the weeds while effectively shielding the crops from the spray.

These and other possible application methods for selectively applying liquid compositions to weeds are discussed in detail in Innovative Methods of Post-Emergence Weed Control, McWhorter C. G, Southern Weed Science Society, 33rd Annual Meeting Proceedings, Jan. 15–17, 1980; Auburn University Printing Service, Auburn, Ala. U.S.A., the teachings of which are incorporated herein by reference in their entirety.

Another possible method of applying liquid compositions of this invention to plants includes controlled droplet application which is also known as the ultra low-volume chemical application. Controlled droplet application involves the production of uniform or nearly uniform spray drops of a predetermined size and the conveyance of these drops with negligible evaporation to a spray target. In particular, this method comprises feeding spray solutions to a rotary atomizer comprising a small disk with serrated edges that disperses liquid into droplets as the disk spins. Different droplet sizes are produced by changing solution flow rates to the spinning disk or changing the speed of rotation of the disk.

Those of skill in the art will recognize that the physical and chemical characteristics of the compound or composition employed will determine to a large extent the particular application method selected therewith.

The aforementioned and other methods for applying liquid compositions to plants are discussed in detail in "Rope Wick Applicator—Tool With A Future", Dale, James E., pp. 3-4, "The Recirculating Sprayer and Roundup ® Herbicide", Derting, Claude W., pp. 5-7, and "C.D.A. Herbicide Application", McGarvey, Frank X., *Weeds Today,* Volume 11, Number 2, pp. 8-9, Late Spring 1980, 309 W. Clark St., Champaign, Ill., the teachings of which are incorporated herein by reference in their entirety.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A process for preparing a compound of the formula

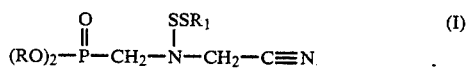

wherein R is selected from the group consisting of phenyl, naphthyl, biphenylyl; or phenyl, naphthyl or biphenylyl substituted with from 1 to 3 substituents independently selected from the group consisting of lower alkyl, lower alkoxy, lower alkylthio, lower alkoxycarbonyl, methylenedioxy, trifluoromethyl, cyano, nitro and halogen; and $R_1$ is independently alkyl, cycloalkyl, aralower alkyl, phenyl, naphthyl, or phenyl, naphthyl or aralower alkyl substituted with from 1 to 3 substituents independently selected from the group consisting of lower alkyl, lower alkoxy, halogen, and trifluoromethyl which comprises reacting a compound of the formula

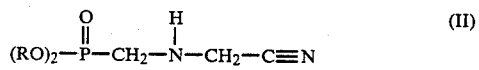

wherein R is as aforedefined with sulfur dichloride in the presence of a hydrogen chloride acceptor to form a compound of the formula

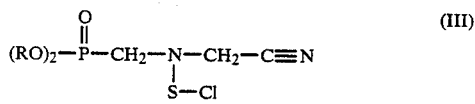

wherein R is as above defined, and reacting said compound of formula (III) with a compound of the formula

to form said compound of formula (I) wherein $R_1$ is as aforedefined in the presence of a hydrogen chloride acceptor.

2. The process of claim 1, wherein R is phenyl.

3. The process of claim 2, wherein said hydrogen chloride acceptor is a tertiary amine.

4. The process of claim 2 wherein said hydrogen chloride acceptor is an amine.

5. The process of claim 3, wherein said tertiary amine is triethylamine.

6. The process of claim 3 wherein said aprotic solvent comprises benzene, toluene, tetrahydrofuran, cyclohexane, methylcyclohexane, hexane, octane, dioxane, ethyl ether, and dichloromethane.

7. The process of claim 3, wherein said aprotic solvent comprises toluene.

8. The process of claim 7, wherein the temperature of the reaction is in the range from about −50° C. to about 100° C.

9. The process of claim 8, wherein the temperature of the reaction is in the range from about −30° C. to about +10° C.

10. The process of claim 1, wherein the reaction of a compound of said formula (II) with a sulphur dichloride is carried out in the presence of an aprotic solvent.

11. The process of claim 1, wherein the reaction of a compound of said formula (III) with a compound of said formula (IV) is carried out in the presence of an aprotic solvent.

12. The process of claim 2, wherein $R_1$ is alkyl.

13. The process of claim 12, wherein $R_1$ is n-octyl.

14. The process of claim 12, wherein $R_1$ is 3-methylbutyl.

15. The process of claim 12, wherein $R_1$ is 1-methylethyl.

16. The process of claim 12, wherein $R_1$ is methyl.

17. The process of claim 12, wherein $R_1$ is 1,1-dimethylethyl.

18. The process of claim 2, wherein $R_1$ is phenyl or phenyl substituted with 1 to 3 substituents selected from the group consisting of lower alkyl, lower alkoxy, halogen and trifluoromethyl.

19. The process of claim 18 wherein $R_1$ is 4-methoxyphenyl.

20. The process of claim 18, wherein $R_1$ is 3-trifluoromethylphenyl.

21. The process of claim 12, wherein $R_1$ is 3-trifluoromethylphenylmethyl.

22. The process of claim 18, wherein $R_1$ is 4-chlorophenyl.

23. The process of claim 2, wherein $R_1$ is naphthyl.

24. The process of claim 2, wherein $R_1$ is cycloalkyl.

25. The process of claim 24, wherein $R_1$ is cyclohexyl.

26. The process of claim 2 wherein $R_1$ is aralower alkyl or aralower alkyl substituted with 1 to 3 substituents selected from the group consisting of lower alkyl, lower alkoxy, halogen, and trifluoromethyl.

* * * * *